(12) United States Patent
Bushnell

(10) Patent No.: US 11,589,761 B2
(45) Date of Patent: Feb. 28, 2023

(54) ELECTRONIC DEVICES HAVING OPTICAL SENSORS WITH CURVED LAMINATED FILMS

(71) Applicant: Apple Inc., Cupertino, CA (US)

(72) Inventor: Tyler S. Bushnell, Mountain View, CA (US)

(73) Assignee: Apple Inc., Cupertino, CA (US)

( * ) Notice: Subject to any disclaimer, the term of this patent is extended or adjusted under 35 U.S.C. 154(b) by 958 days.

(21) Appl. No.: 16/276,240

(22) Filed: Feb. 14, 2019

(65) Prior Publication Data

US 2020/0260971 A1 Aug. 20, 2020

(51) Int. Cl.
| | |
|---|---|
| *A61B 5/024* | (2006.01) |
| *A61B 5/00* | (2006.01) |
| *G04G 17/08* | (2006.01) |
| *G04G 21/02* | (2010.01) |

(52) U.S. Cl.
CPC .......... *A61B 5/02427* (2013.01); *A61B 5/681* (2013.01); *G04G 17/08* (2013.01); *G04G 21/025* (2013.01)

(58) Field of Classification Search
CPC .................................................... G06F 1/1637
See application file for complete search history.

(56) References Cited

U.S. PATENT DOCUMENTS

| | | | |
|---|---|---|---|
| 5,254,388 A | 10/1993 | Melby et al. | |
| 6,398,370 B1 | 6/2002 | Chiu et al. | |
| 2008/0186558 A1* | 8/2008 | Lee | G02B 6/04 359/227 |
| 2011/0004106 A1* | 1/2011 | Iwamiya | A61B 5/02438 600/476 |
| 2014/0107493 A1* | 4/2014 | Yuen | A61B 5/0022 600/479 |
| 2016/0058312 A1 | 3/2016 | Han et al. | |
| 2016/0310027 A1 | 10/2016 | Han | |
| 2017/0086689 A1 | 3/2017 | Shui et al. | |
| 2017/0164848 A1 | 6/2017 | Nadeau et al. | |
| 2017/0354335 A1* | 12/2017 | Bower | A61B 5/6833 |
| 2018/0279956 A1 | 10/2018 | Waydo et al. | |
| 2020/0045155 A1* | 2/2020 | Ha | G02B 5/0808 |

* cited by examiner

*Primary Examiner* — Nan-Ying Yang
(74) *Attorney, Agent, or Firm* — Treyz Law Group, P.C.; G. Victor Treyz; Tianyi He

(57) ABSTRACT

An electronic device such as a wearable device may have an optical sensor. The optical sensor may have a light source such as one or more visible-light light-emitting diodes or other light-emitting devices and may have a light detector formed from one or more photodetectors. The wearable device may have a wearable housing in which the optical sensor is mounted. During operation, light from the light source may pass through a transparent portion of the housing, may reflect from an external object such as a wrist or other body part of a user, and may be received by the photodetectors after passing through light control members. The light control members may be arranged in a ring with a center and may have curved shapes with concave surfaces that face the center. Each light control member may be formed from a stack of laminated bent light control films.

20 Claims, 7 Drawing Sheets

ELECTRONIC DEVICES HAVING OPTICAL SENSORS WITH CURVED LAMINATED FILMS

FIELD

This relates generally to electronic devices, and, more particularly, to electronic devices with optical components.

BACKGROUND

Electronic devices may include sensors. For example, an optical sensor may be used in a wristwatch to measure a user's heart rate.

It can be challenging to incorporate sensors such as optical sensors into electronic devices. For example, optical components for providing an electronic device with desired functionality may be too bulky or unattractive to incorporate into the electronic device.

SUMMARY

An electronic device such as a wearable electronic device may have an optical sensor. The optical sensor may have a light source such as one or more visible-light light-emitting diodes and may have a light detector formed from one or more photodetectors. The optical sensor may be used as a hear rate sensor or other sensor in the electronic device.

The electronic device may have a housing in which the optical sensor is mounted. During operation, light from the light source may pass through a transparent portion of the housing, may reflect from an external object such as a wrist or other body part of a user, and may be received by the photodetectors after passing through light control members. Analysis of the received light may reveal biometric information on the user. The light control members may help reduce stray light signals.

The light control members may be arranged in a ring. The light control members may each have a curved shape with a concave surface that faces the center of the ring. Each light control member may be formed from a stack of laminated bent light control films. The light control films for the stack may be pressed into desired bent shapes using a lamination tool with curved surfaces.

DETAILED DESCRIPTION

An electronic device may have an optical sensor. The optical sensor may include a light source and a light detector. The light detector may include photodetectors or other light detector elements that measure light from the light source after the light has passed through a user's wrist or other body part. In this type of arrangement, the light source and detector may form a heart rate sensor (e.g., a photoplethysmography heart rate sensor) or other biometric sensor. Configurations in which optical sensors are used for making other types of arrangements may also be used, if desired.

To reduce the impact of stray light when making measurements of a user's body through a transparent housing wall, light control members formed from stacks of light control film may be interposed between the housing wall and the light detectors. The light control members may be curved members formed by laminating together bent light control films.

Figure 1:
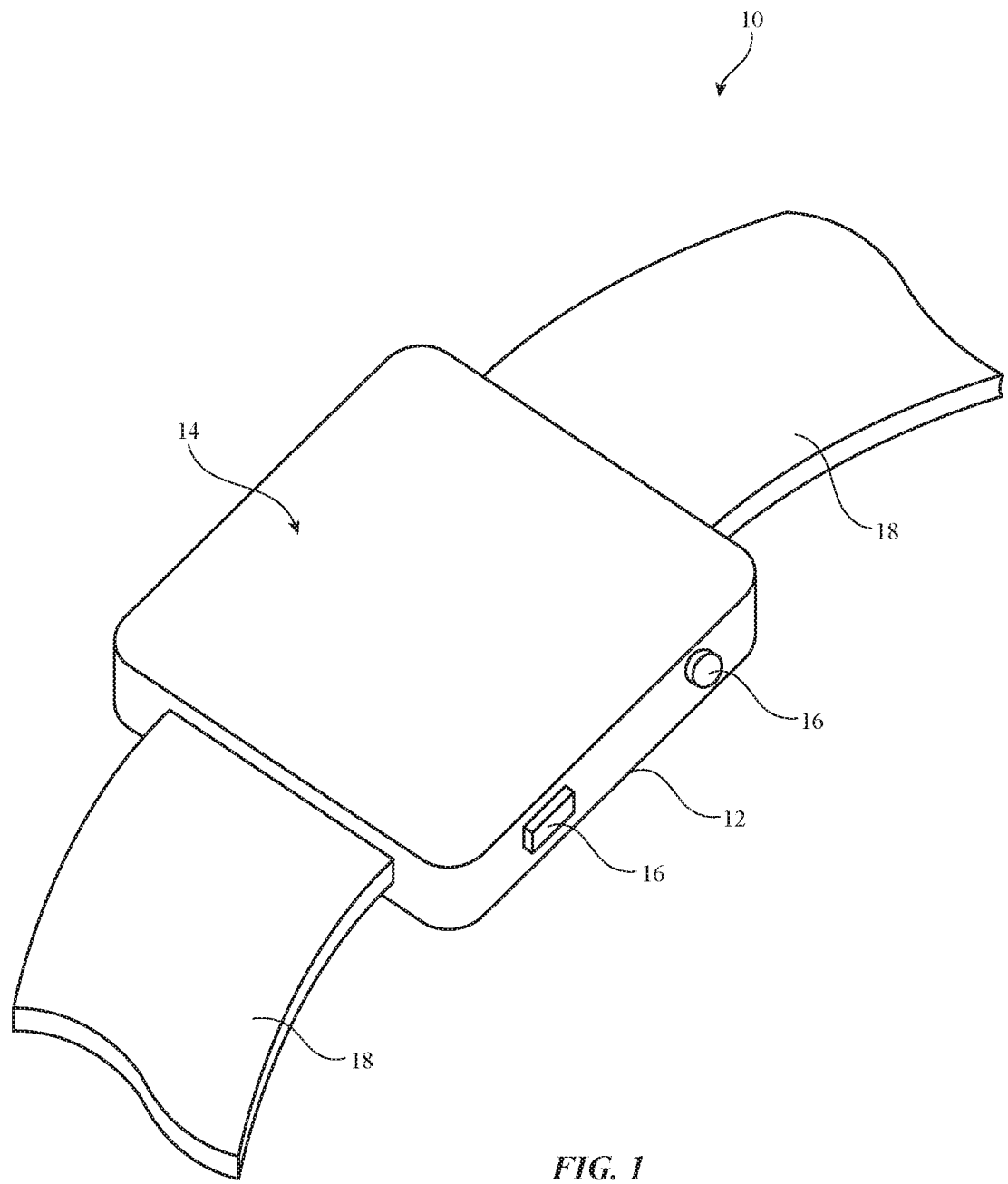
FIG. 1 is perspective view of an illustrative electronic device in accordance with an embodiment.

An illustrative electronic device of the type that may include an optical sensor is shown in FIG. 1. Device 10 may be a laptop computer, a computer monitor containing an embedded computer, a tablet computer, a desktop computer, a cellular telephone, a media player, or other handheld or portable electronic device, a smaller device such as a wristwatch device, a wristband device, a pendant device, a headphone or earpiece device, a head-mounted device such as glasses, goggles, a helmet, or other equipment worn on a user's head, or other wearable or miniature device, a television, a computer display that does not contain an embedded computer, a gaming device, a navigation device, an embedded system such as a system in which equipment is mounted in a kiosk, in an automobile, airplane, or other vehicle, a removable external case for electronic equipment, an accessory such as a remote control, computer mouse, track pad, wireless or wired keyboard, or other accessory, and/or equipment that implements the functionality of two or more of these devices. In the illustrative configuration of FIG. 1, device 10 is a wearable electronic device such as a wristwatch. This configuration may sometimes be described herein as an example. Other types of electronic device may include optical sensors if desired.

As shown in FIG. 1, device 10 may have a housing such as housing 12. Housing 12 may be formed from materials such as polymer, glass, metal, crystalline materials such as sapphire, ceramic, fabric, foam, wood, other materials, and/or combinations of these materials. Input-output devices such as one or more buttons 16 may be mounted on housing 12. During operation, a user may press buttons 16, may turn buttons 16, or may otherwise use buttons 16 to provide device 10 with input.

User input may also be gathered using touch sensors, a microphone, a force sensor, an accelerometer, and/or other input-output devices. Output may be provided to a user with speakers, haptic output devices (e.g., a vibrator or other electromagnetic actuator), status indicator lights, and/or other output devices.

If desired, device 10 may have an output device such as display 14. Display 14 has an array of pixels for displaying images to users. Display 14 may be a light-emitting diode display (e.g., an organic light-emitting diode display or a display with a pixel array having light-emitting diodes formed from crystalline semiconductor dies), a liquid crystal display, or other display. Display 14 may include a two-dimensional capacitive touch sensor or other touch sensor for gathering touch input. A force sensor in device 10 may be coupled between display 14 and housing 12 so that a user may supply force input by pressing against display 14.

Device 10 may have structures that are configured to allow device 10 to be worn on a wrist or other body part of a user. For example, device 10 may have wrist strap 18. Strap 18, which may sometimes be referred to as a band, may have one or more segments that are configured to allow device 10 to be worn on a user's wrist.

Figure 2:
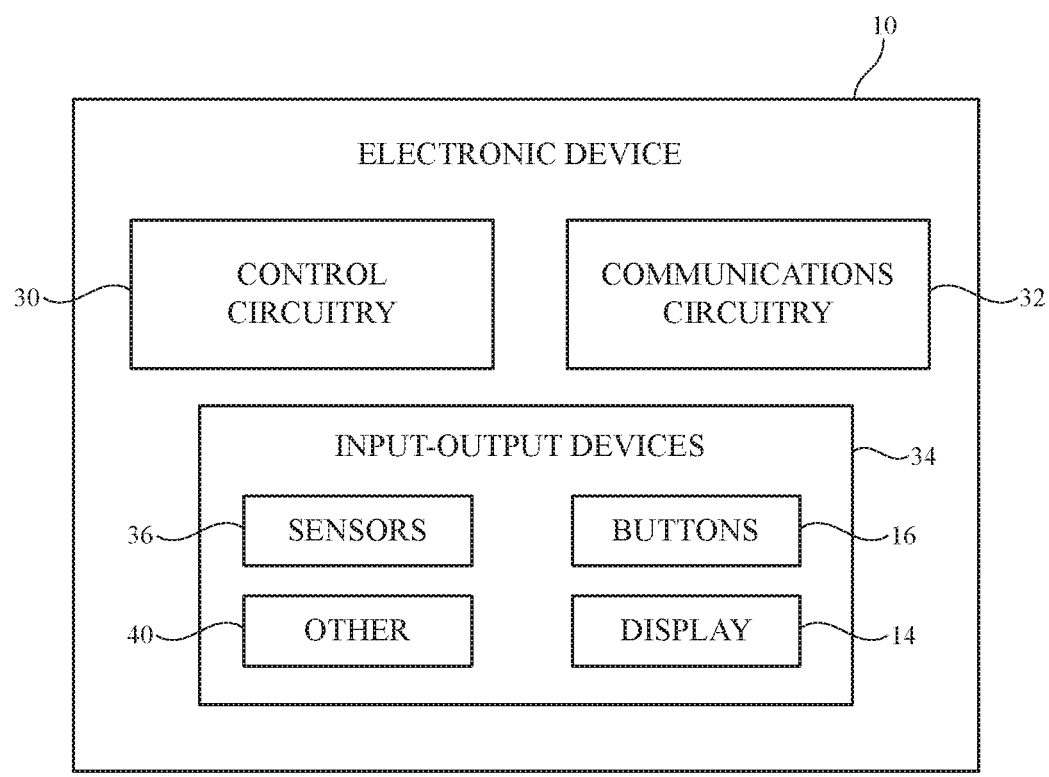
FIG. 2 is a schematic diagram of an illustrative electronic device in accordance with an embodiment.

A schematic diagram of an illustrative electronic device is shown in FIG. 2. As shown in FIG. 2, device 10 may include control circuitry 30, communications circuitry 32, and input-output devices 34.

Control circuitry 30 may include storage and processing circuitry for supporting the operation of device 10. The storage and processing circuitry may include storage such as nonvolatile memory (e.g., flash memory or other electrically-programmable-read-only memory configured to form a solid state drive), volatile memory (e.g., static or dynamic random-access-memory), etc. Processing circuitry in control circuitry 30 may be used to gather input from sensors and other input devices and may be used to control output devices. The processing circuitry may be based on one or more microprocessors, microcontrollers, digital signal processors, baseband processors and other wireless communications circuits, power management units, audio chips, application specific integrated circuits, etc.

To support communications between device 10 and external electronic equipment, control circuitry 30 may communicate using communications circuitry 32. Communications circuitry 32 may include antennas, radio-frequency transceiver circuitry, and other wireless communications circuitry and/or wired communications circuitry. Circuitry 32, which may sometimes be referred to as control circuitry and/or control and communications circuitry, may, for example, support wireless communications using wireless local area network links, near-field communications links, cellular telephone links, millimeter wave links, and/or other wireless communications paths.

Input-output devices 34 may be used in gathering user input, in gathering information on the environment surrounding the user, and/or in providing a user with output. Devices 34 may include sensors 36. Sensors 36 may include force sensors (e.g., strain gauges, capacitive force sensors, resistive force sensors, etc.), audio sensors such as microphones, capacitive touch sensors, capacitive proximity sensors, other touch sensors, ultrasonic sensors, sensors for detecting position, orientation, and/or motion (e.g., accelerometers, magnetic sensors such as compass sensors, gyroscopes, and/or inertial measurement units that contain some or all of these sensors), muscle activity sensors (EMG), heart rate sensors, electrocardiogram sensors, and other biometric sensors, radio-frequency sensors (e.g., radar and other ranging and positioning sensors), humidity sensors, moisture sensors, and/or other sensors.

Input-output devices 34 may include optical components such as light-emitting diodes (e.g., for camera flash or other blanket illumination, etc.), lasers such as vertical cavity surface emitting lasers and other laser diodes, laser components that emit multiple parallel laser beams (e.g., for three-dimensional sensing), lamps, and light sensing components such as photodetectors and digital image sensors. For example, sensors 36 in devices 34 may include depth sensors (e.g., structured light sensors and/or depth sensors based on stereo imaging devices that can optically sense three-dimensional shapes), optical sensors such as self-mixing sensors and light detection and ranging (lidar) sensors that gather time-of-flight measurements and/or other measurements to determine distance between the sensor and an external object and/or that can determine relative velocity, monochromatic and/or color ambient light sensors that can measure ambient light levels, proximity sensors based on light (e.g., optical proximity sensors that include light sources such as infrared light-emitting diodes and/or lasers and corresponding light detectors such as infrared photodetectors that can detect when external objects are within a predetermined distance), optical sensors such as visual odometry sensors that gather position and/or orientation information using images gathered with digital image sensors in cameras, gaze tracking sensors, visible light and/or infrared cameras having digital image sensors configured to gather image data, optical sensors for measuring ultraviolet light, and/or other optical sensor components (e.g., light sensitive devices and, if desired, light sources), photodetectors coupled to light guides, associated light emitters, and/or other optical components (one or more light-emitting devices, one or more light-detecting devices, etc.).

To make biometric measurements, sensors 36 may include an optical sensor that emits light into a user's body and detects backscattered (reflected) light from the user's body. This type of optical sensor may, as an example, serve as a heart rate sensor.

In addition to sensors 36, input-output devices 34 may include user input devices such as buttons 16 and visual output devices such as display 14. Input-output devices 34 may also include other devices 40. Devices 40 may include, for example, light-based output devices other than display 14 that are used to provide visual output to a user. The light-based output devices may include one or more light-emitting diodes, one or more lasers, lamps, electroluminescent devices, and/or other light emitting components. The light-based output devices may form status indicator lights. If desired, the light-based output devices may include illuminated icons (e.g., backlight symbols associated with power indicators, battery charge indicators, wireless signal strength indicators, notification icons, etc.).

If desired, devices 40 may include speakers and other audio output devices, electromagnets, permanent magnets, structures formed from magnetic material (e.g., iron bars or other ferromagnetic members that are attracted to magnets such as electromagnets and/or permanent magnets), batteries, etc. Devices 40 may also include power transmitting and/or receiving circuits configured to transmit and/or receive wired and/or wireless power signals. Devices 40 may include microphones for gathering voice commands, touch sensor input devices, accelerometers for gathering user input gestures such as tap gestures, and/or other devices for gathering user input. Devices 40 may also include output components such as haptic output devices and other output components (e.g., electromagnetic actuators or other actuators that can vibrate to provide a user with a haptic alert and/or haptic feedback associated with operation of a touch sensor or other input devices).

Figure 3:
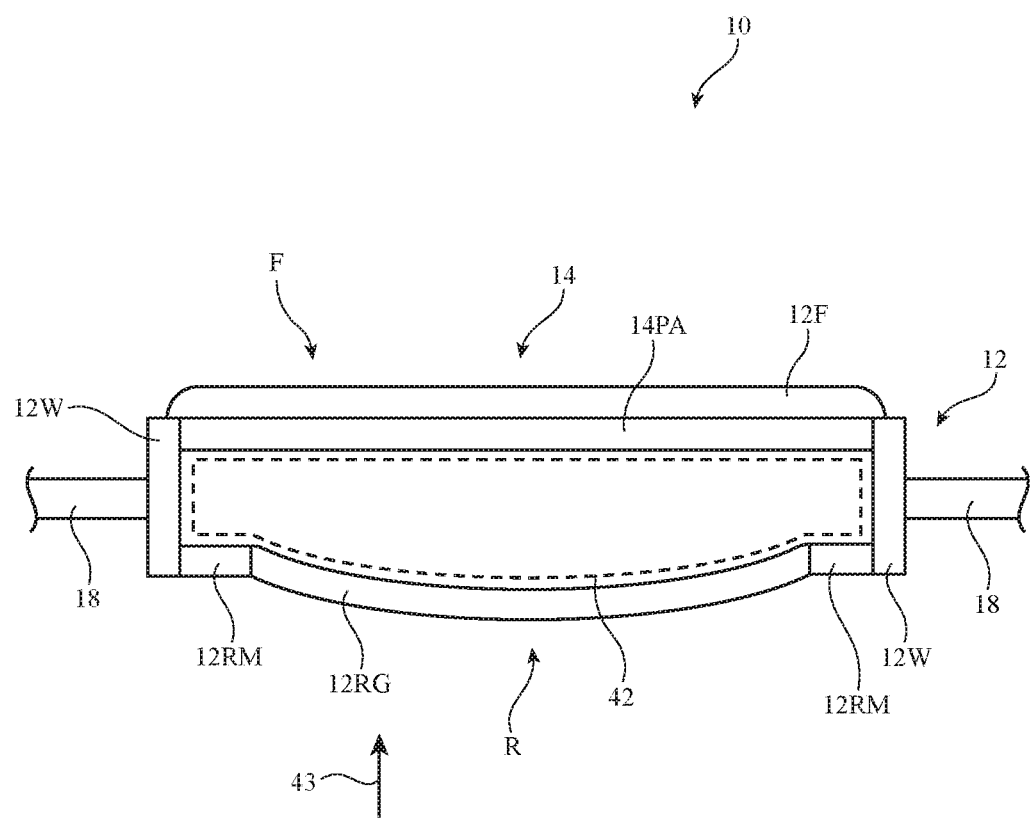
FIG. 3 is a cross-sectional side view of an illustrative electronic device in accordance with an embodiment.

A cross-sectional side view of device 10 of FIG. 1 is shown in FIG. 3. As shown in FIG. 3, housing 12 may have one or more portions such as sidewall portions 12W, front portion 12F on front face F of device 10, and rear portions 12RM and 12RC on rear face R of device 10. Straps 18 may be coupled to sidewalls in housing 12 such as sidewall portions 12W. These portions may be formed from metal (e.g., aluminum, stainless steel, or other metals) or may be formed from polymer, glass, ceramic, and/or other materials.

Some or all of housing 12 may be transparent. For example, housing portion 12F may be a transparent display cover layer that overlaps and protects display pixel array 14PA of display 14. Housing portion 12F may be formed from sapphire or other crystalline material, glass, polymer, transparent ceramic, and/or other transparent material. Rear portion 12RG may have a circular shape (e.g., a circular outline) or other suitable shape when rear face R is viewed in direction 43. Portion 12RG may be formed from transparent material such as sapphire or other crystalline material, glass, polymer, transparent ceramic, and/or other transparent material. This allows optical sensors to operate through rear housing portion 12RG. Portion 12RM, which may be used to support portion 12RG and to couple portion 12RG to portion 12W and the rest of housing 12, may be formed form opaque material (e.g., metal such as aluminum, stainless steel, or other metals, opaque polymer, or other opaque materials) or may be formed from a transparent material.

If desired, opaque structures such as coatings of opaque ink, metal, or other opaque coating material may be provided on the surface of a housing structure that is otherwise transparent. For example, portions of a transparent member forming rear housing portion 12RG may have an interior surface that is covered with opaque masking material to help hide internal components 42 from view. Windows may be formed in the opaque masking material or other opaque structures in housing 12 (e.g., an opaque rear housing wall) to allow light to pass out of and into device 10. Components 42 in the interior of device 10 may include integrated circuits, discrete components, a battery, wireless circuit components such as a wireless power coil, and/or other components (see, e.g., control circuitry 30, communications circuitry 32, and input-output devices 34 of FIG. 2).

Figure 4:
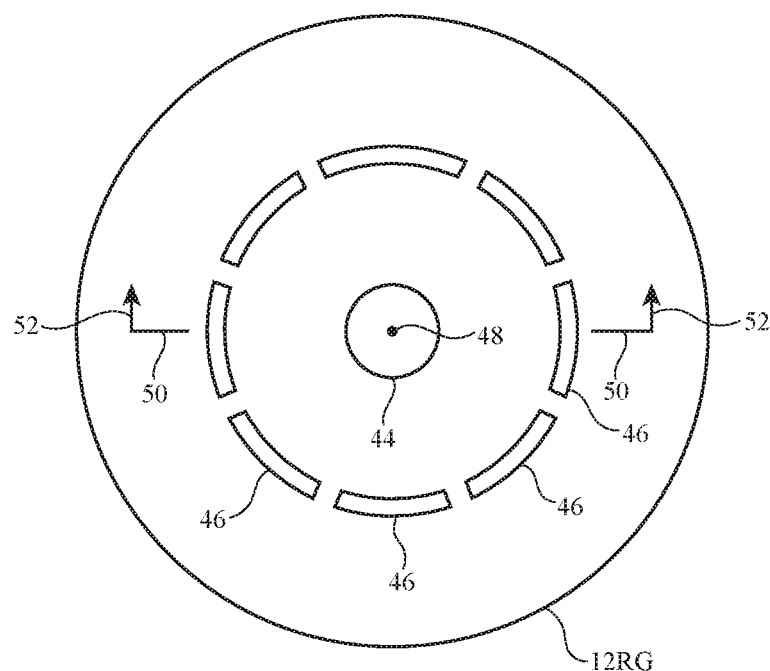
FIG. 4 is a rear view of a transparent housing structure on the rear face of an electronic device showing illustrative locations for light source and light detector components in accordance with an embodiment.

Rear housing portion 12RG or other transparent housing structures in housing 12 (e.g., transparent windows in opaque housing walls, transparent housing wall structures, etc.) may overlap a light source and light detector that form an optical sensor such as a heart rate sensor. FIG. 4 is a rear view of rear housing portion 12RG of device 10 of FIG. 3 viewed in direction 43 of FIG. 3. As shown in FIG. 4, rear housing portion 12RG may, if desired, have a circular shape and may be characterized by a central point such as center point 48.

Optical sensor components may be mounted within the interior of device 10 under rear housing portion 12RG. For example, light-emitting components that form a light source may be located behind rear housing portion 12RG in one or more regions such as region 44 and light detector components that form a light detector may be located behind rear housing portion 12RG in one or more regions such as regions 46. In the example of FIG. 4, light emission region 44 is a circular region aligned with the center of rear housing portion 12RG (center point 48) and there are eight non-contiguous light detection regions 46 arranged in a ring (circle) around light emission region 44.

Regions 46 may, as an example, be formed from eight discrete segments of a ring-shaped area that has a center aligned with center point 48 (e.g., a ring in which regions 46 are separated by gaps). Other numbers of ring segments may be include in regions 46 if desired. For example, there may be two regions 46, four regions 46, at least six regions 46, fewer than 12 regions 46, etc. Arrangements may also be used in which different shapes of light emission region(s) and/or different shapes of light detection region(s) are included in device 10 to allow light for an optical sensor to be emitted and detected through housing 12.

Figure 5:
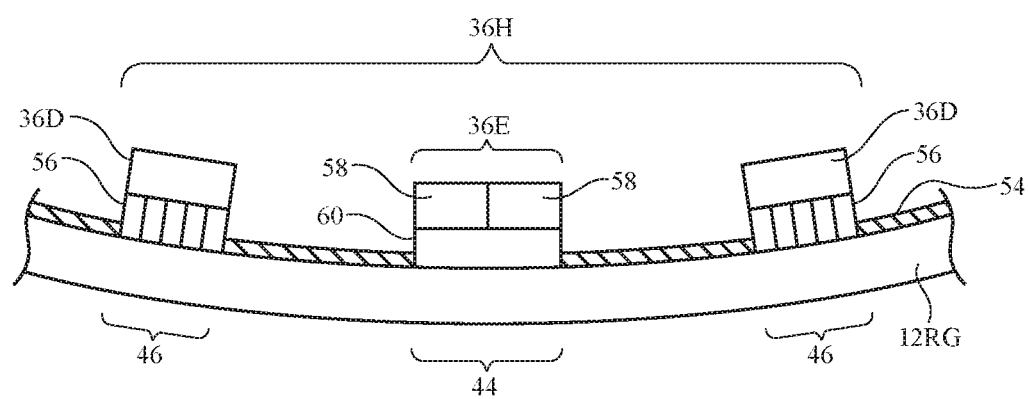
FIG. 5 is a cross-sectional side view of an illustrative portion of an electronic device with an optical sensor in accordance with an embodiment.

FIG. 5 is a cross-sectional side view of device 10 of FIG. 4 taken along line 50 and viewed in direction 52. As shown in FIG. 5, electrical components are provided on the interior side of housing portion 12RG for forming optical sensor 36H. Optical sensor 36H may be a biometric sensor such as a heart rate sensor that operates by measuring reflected light from a user's wrist or other body part or may be any other type of optical sensor. The electrical components for forming optical sensor 36H may be located on the interior side of rear housing portion 12RG (e.g., a sapphire member, glass member, polymer member, or other rear housing wall structure with a circular shape or other suitable shape) in alignment with regions 44 and 46. Opaque masking structures such as opaque layer 54 may be formed on some of the inner surface of rear housing portion 12RG (e.g., in areas that are not overlapped by the optical components of sensor 36H) to hide internal structures from view from the exterior of device 10. Rear housing portion 12RG or at least the parts of portion 12RG that are overlapped by the optical components of sensor 36H may be transparent to allow light to be emitted from the interior of device 10 and to allow light from the exterior of device 10 to pass to the interior of device 10.

The electrical components of optical sensor 36H may include light source 36E and light detector 36D. Light source 36E may have one or more light-emitting devices 58 such as light-emitting diodes and/or laser diodes. Light source 36E may, as an example, have a pair of light-emitting devices 58 such as first and second visible-light light-emitting diodes that are configured to emit green light or other visible light. Arrangements in which light source 36E emits infrared light and/or ultraviolet light may also be used. Light detector 36D may include eight photodetectors each of which is associated with a respective one of the eight regions 46 of FIG. 4 or may include fewer photodetectors or more photodetectors. The photodetectors may, as an example, each be formed from a respective photodiode that overlaps a respective one of regions 46. Configurations in which each light detection region 46 uses multiple photodetectors may also be used. Light detector 36D may, in general, have at least two photodetectors, at least five photodetectors, at least 10 photodetectors, fewer than 15 photodetectors, eight photodetectors, fewer than seven photodetectors, etc.

An optical component such as optical component 60 may be interposed between the inner surface of rear housing portion 12RG and light emitter 36E. Optical component 60 may include one or more lenses and/or other components for performing functions such as controlling the orientation of emitted light. During operation, control circuitry 30 may use light-emitting device(s) 58 of light emitter 36E to emit light. This light passes through optical structure 60 and a transparent portion of housing 12 in region 44 to illuminate an external object such as a user's wrist or other body part. Some of the emitted light is reflected back to device 10. Control circuitry 30 may use light detector 36D to measure the reflected light and to process signal measurements to determine a user's heart rate and/or to produce other sensor data (e.g., other biometric information).

Optical sensor 36H may include optical structures such as light control members 56 (sometimes referred to as optical components or light control structures). Light control members 56 may each be formed from a stack of laminated light control films. Each light control member 56 may be interposed between the inner surface of rear housing portion 12RG and a respective one or more of the photodetectors in light detector 36D. For example, each light control member 56 may pass light to a respective photodetector.

Light control members 56 may be used to help narrow the angles of acceptance of the photodetectors and thereby reduce stray optical signals that might otherwise be detected by the photodetectors. In this way, the presence of light control members 56 may enhance the performance of optical sensor 36H.

Figure 6:
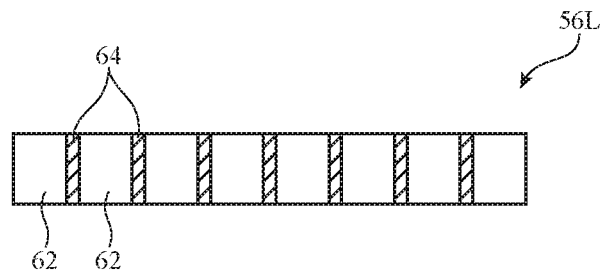
FIG. 6 is a cross-sectional side view of an illustrative light control film that may be used in forming a light control member in accordance with an embodiment.

The light control members may be formed from laminated layers of light control film. An illustrative light control film is shown in FIG. 6. As shown in FIG. 6, light control film 56L may include a layer of transparent material such as polymer 62. Film 56L may also include a set of louver structures such as louvers 64 that block off-axis light while allowing light that is propagating parallel to the louvers to pass.

Figure 7:
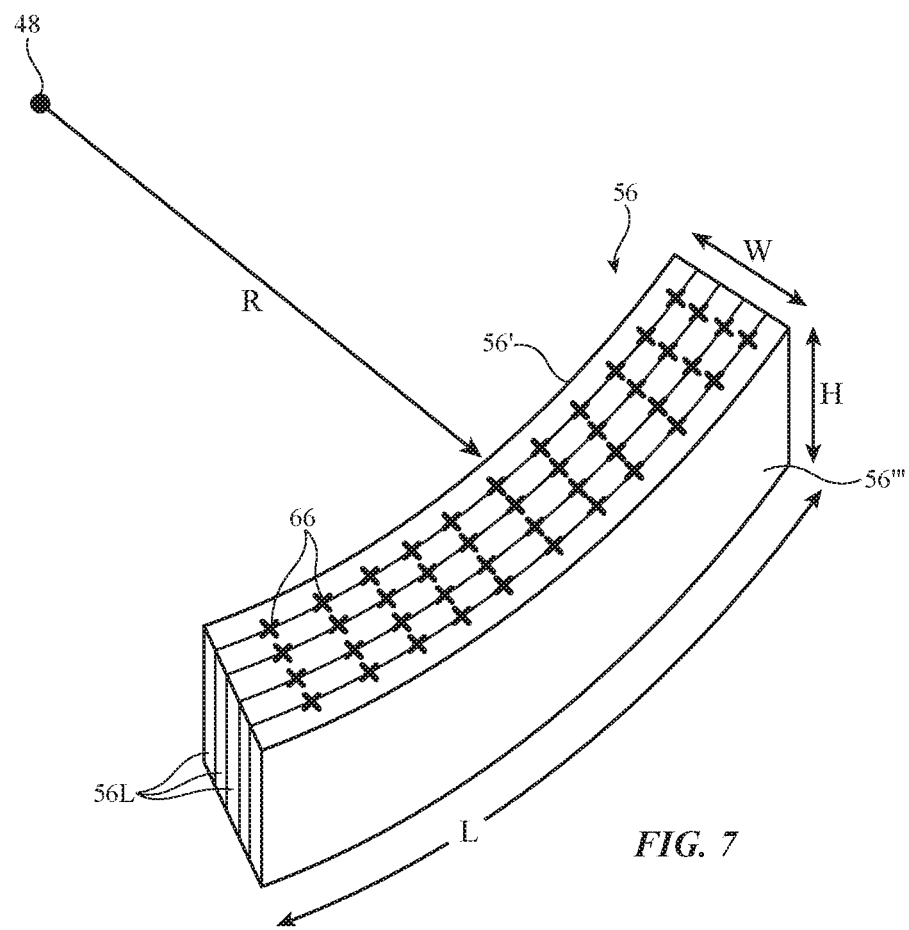
FIG. 7 is a perspective view of an illustrative light control member formed from a stack of laminated bent light control films in accordance with an embodiment.

FIG. 7 is a perspective view of an illustrative light control member. As shown in FIG. 7, light control member 56 may be formed from a set of laminated light control films 56L (sometimes referred to as light control film layers or light control layers). The stack of laminated light control films 56L for light control member 56 may have a curved shape with a concave surface 56' facing center point 48 and an opposing convex surface facing away from center point 48. The radius of curvature of member 56 (e.g., the distance R of surface 56' or the distance of surface 56" from center point 48) may be at least 2 mm, at least 4 mm, at least 5 mm, at least 1 cm, at least 2 cm, at least 3 cm, less than 4 cm, less than 2.5 cm, less than 1.8 cm, less than 0.9 cm, or other suitable value. The length L of member 56 measured along the curved outer edge of member 56 may be at least 1 mm, at least 2 mm, at least 3 mm, less than 6 m, less than 5 mm, less than 4 mm, less than 2 mm, or other suitable value. The height H (distance from the inner surface of housing portion 12RW) of member 56 may be at least 0.05 mm, at least 0.1 mm, at least 0.2 mm, at least 0.3 mm, less than 1 mm, less than 0.5 mm, less than 0.25 mm, less than 0.15 mm, or other suitable value. The width W of member 56 (e.g., the distance between opposing curved surfaces 56' and 56") may be at least 0.5 mm, at least 0.9 mm, at least 1 mm, at least 2 mm, less than 2.5 mm, less than 1.5 mm, less than 1.2 mm, less than 0.6 mm, or other suitable value.

There may be eight members 56 of the type shown in FIG. 7 arranged in a circle (e.g., there may be a ring of members 56 overlapping eight respective regions 46 of the type shown in FIG. 4 that are separated from each other by gaps) or members 56 may otherwise be mounted in housing 12 between housing 12 and the photodetectors of light detector 36D. There may be any suitable number of films 56L in member 56 (e.g., at least 5, a least 10, at least 20, fewer than 25, fewer than 15, fewer than 8, etc.). The sheets of polymer forming films 56L may be at least 20 microns thick, at least 50 microns thick, at least 80 microns thick, less than 400 microns in thickness, less than 200 microns in thickness, less than 100 microns in thickness, less than 50 microns in thickness, or other suitable thickness. A respective layer of material 66 may be interposed between each pair of adjacent films 56L in member 56. Material 66 may include, for example, adhesive, dye, pigment, metal, polymer, and/or other material. As an example, a layer of adhesive may be interposed between each pair of adjacent films 56L to attach films 56L together to form light control member 56.

The curved shape of light control members 56 allows light control members 56 to form a multi-segment ring of light control members for light detector 36D (e.g., to form a set of light control members such as a ring of light control members in respective regions such as regions 46 of FIG. 4) while reducing undesired light leakage from member 56. To form the curved shape of light control members 56, films 56L may be bent during lamination (e.g., while heat and/or pressure is used to join films 56L together to form member 56).

Figure 8:
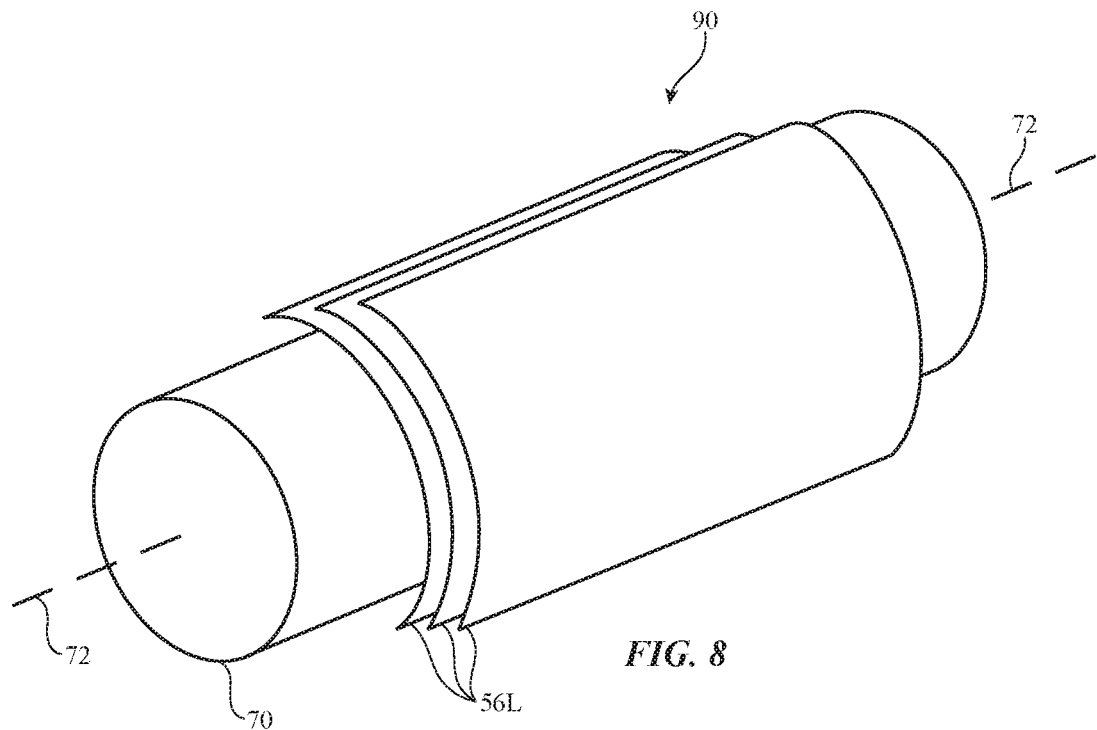
FIG. 8 is a perspective view of an illustrative tool for bending light control films and laminating the bent light control films together in accordance with an embodiment.

FIG. 8 is a perspective view of an illustrative lamination tool 90 for forming curved light control members 56. As shown in FIG. 8, lamination tool member 70 may have a curved outer surface (e.g., member 70 may be a cylinder that is symmetric about rotational axis 72). Films 56L (and intervening adhesive layers) may be pressed against the outer surface of member 70 during lamination (e.g., using a pressing member). Using heat and/or pressure or other lamination techniques (e.g., ultraviolet curable lamination adhesive), films 56L may be bent about axis 72 while being attached to each other to form a curved laminated stack of films.

Figure 9:
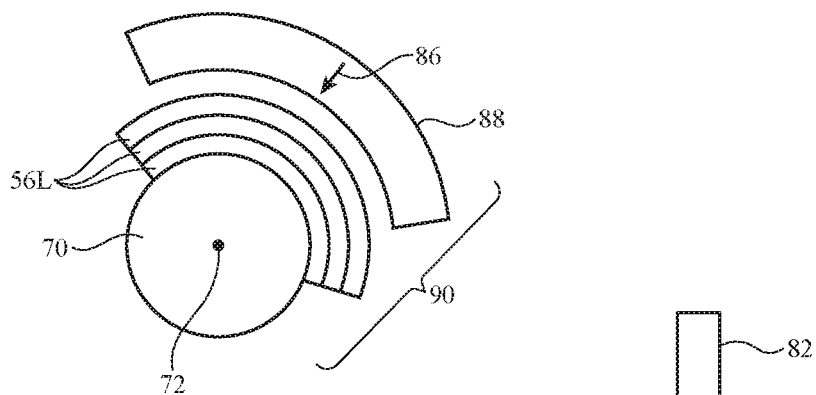
FIG. 9 is an end view of the illustrative tool of FIG. 8 and a set of bent light control films that are being laminated using the tool in accordance with the present invention.

FIG. 9 is a cross-sectional end view of member 70 and films 56L of FIG. 8 showing how pressing member 88 of lamination tool 90 may be moved in direction 86 to bend films 56L while laminating films 56L together. After forming a set of laminated films 56L with a desired curvature, members 56 may be cut from the laminated films along lines 80 using cutting tool 82 of FIG. 10 (e.g., a laser, blade, or other cutter) to form curved members such as curved light control member 56 of FIG. 7. Members 56 may then be installed in device 10 and coupled to housing 12 and photodetectors in detector 36D (e.g., using adhesive and/or other mounting structures).

Figure 10:
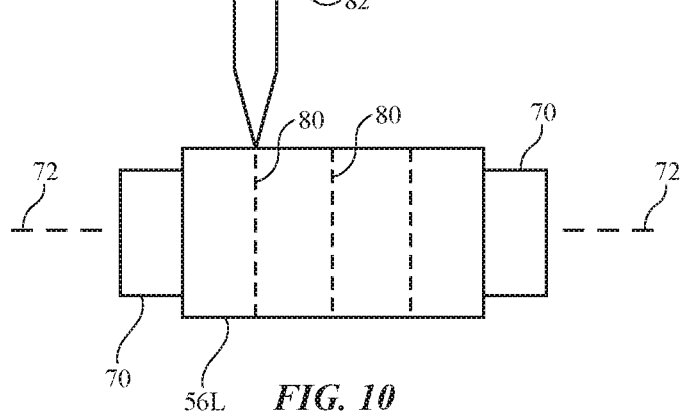
FIG. 10 is a side view of the illustrative tool of FIGS. 8 and 9 showing how a cutting tool can be used to separate laminated sections of light control films from each other to form curved light control members in accordance with an embodiment.
Figure 11:
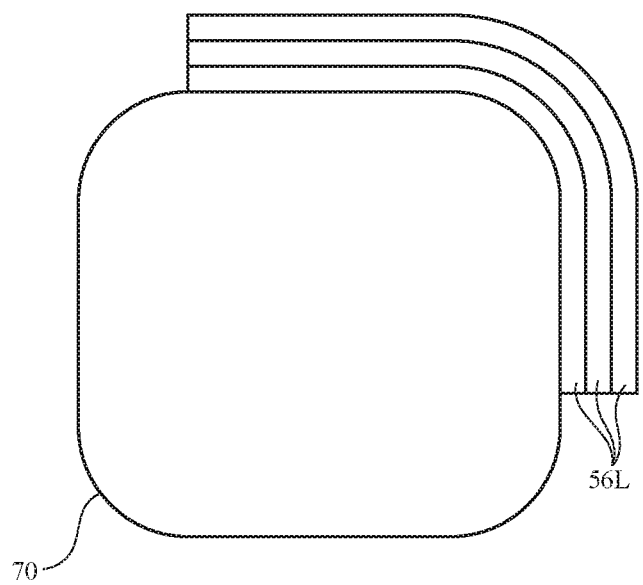
FIG. 11 is an end view of another illustrative tool for laminating light control films in accordance with an embodiment.

In the example of FIGS. 8, 9, and 10, the lamination tool has a cylindrical inner member with a cylindrical surface against which films 56L are pressed to bend films 56L and form a stack of laminated bent films for member 56. Other lamination tool shapes may be used, if desired (e.g., shapes with triangular cross-sectional shapes, rectangular cross-sectionals shapes, shapes with square cross sections and rounded corners such as the shape of illustrative tool member 70 FIG. 11, and/or other suitable shapes).

Light control members 56 may be used to route light between the exterior of device 10 and photodetectors in light detector 36D of optical sensor 36H or may be used to route light to or from any other optical device in input-output devices 34 (e.g., an ambient light sensor, etc.).

As described above, one aspect of the present technology is the gathering and use of information such as sensor information (e.g., optical sensor information). The present disclosure contemplates that in some instances, this gathered data may include personal information data that uniquely identifies or can be used to contact or locate a specific person. Such personal information data can include demographic data, location-based data, telephone numbers, email addresses, twitter ID's, home addresses, data or records relating to a user's health or level of fitness (e.g., vital signs measurements, medication information, exercise information), date of birth, eyeglasses prescription, username, password, biometric information, or any other identifying or personal information.

The present disclosure recognizes that the use of such personal information, in the present technology, can be used to the benefit of users. For example, the personal information data can be used to deliver targeted content that is of greater interest to the user. Accordingly, use of such personal information data enables users to calculated control of the delivered content. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the United States, collection of or access to certain health data may be governed by federal and/or state laws, such as the Health Insurance Portability and Accountability Act (HIPAA), whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, the present technology can be configured to allow users to select to "opt in" or "opt out" of participation in the collection of personal information data during registration for services or anytime thereafter. In another example, users can select not to provide certain types of user data. In yet another example, users can select to limit the length of time user-specific data is maintained. In addition to providing "opt in" and "opt out" options, the present disclosure contemplates providing notifications relating to the access or use of personal information. For instance, a user may be notified upon downloading an application ("app") that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data.

The foregoing is illustrative and various modifications can be made to the described embodiments. The foregoing embodiments may be implemented individually or in any combination.

What is claimed is:

1. An electronic device, comprising:
   a housing;
   a stack of laminated bent light control films, wherein the stack of laminated bent light control films has opposing first and second curved surfaces separated from each other by a width of the stack and wherein the stack of laminated bent light control films has an additional surface that extends between the first and second curved surfaces and is separated from the housing by a height of the stack; and
   a light detector configured to detect light that has passed through the housing and the stack of laminated bent light control films along the height.

2. The electronic device defined in claim 1 further comprising a light source, wherein the housing comprises a wristwatch housing having a transparent rear wall portion, wherein the stack of laminated bent light control films forms a curved light control member, wherein the electronic device further comprises a heart rate sensor that includes the light detector and the light source, wherein the light source is configured to emit light through the transparent rear wall portion, and wherein the light detector comprises a photodiode that is configured to detect the emitted light after the emitted light has reflected off of a wrist.

3. The electronic device defined in claim 1 wherein the stack of laminated bent light control films comprises layers of adhesive, wherein each layer of adhesive is interposed between a respective pair of adjacent bent light control films in the stack of laminated bent light control films, and wherein each bent light control film includes a layer of polymer with louvers.

4. The electronic device defined in claim 1 wherein the housing has a transparent rear wall portion with a circular outline and a center, wherein the first curved surface faces the center, and wherein the second curved surface faces away from the center.

5. The electronic device defined in claim 1 further comprising a light source, wherein the light source and the light detector form an optical sensor.

6. The electronic device defined in claim 5 wherein the light source comprises at least one visible-light light-emitting diode.

7. A wristwatch, comprising:
a wristwatch housing having opposing front and rear faces;
a display at the front face;
an optical sensor at the rear face, wherein the optical sensor comprises a light source and a light detector; and
laminated bent light control films, wherein each light control film in the laminated bent light control films has a curvature and extends from the wristwatch housing to the light detector and wherein light from the light source passes through the laminated bent light control films to the light detector.

8. The wristwatch defined in claim 7 wherein the laminated bent light control films form curved light control members.

9. The wristwatch defined in claim 8 wherein the wristwatch housing has a transparent portion at the rear face and wherein the light from the light source passes through the transparent portion.

10. The wristwatch defined in claim 9 wherein the transparent portion has a circular outline and a center and wherein the curved light control members each have a concave curved surface facing the center.

11. The wristwatch defined in claim 10 wherein the light detector comprises photodetectors and wherein each photodetector receives the light that has passed through the laminated bent light control films of a respective one of the curved light control members.

12. The wristwatch defined in claim 11 wherein the light source comprises a visible-light light-emitting diode.

13. The wristwatch defined in claim 8 wherein the curved light control members are arranged in a ring and are separated from each other by gaps.

14. An electronic device, comprising:
a ring of optical structures surrounding a center point, each optical structure including a stack of bent light control films having a curved inner surface facing the center point, a curved outer surface facing away from the center point, and a top surface that extends between the curved inner surface and the curved outer surface; and
a light detector configured to detect light that has passed through the top surfaces of the ring of optical structures.

15. The electronic device defined in claim 14 further comprising a light source, wherein the light source emits light that is detected by the light detector.

16. The electronic device defined in claim 15 further comprising a wearable housing, wherein the light source and light detector form an optical sensor in the wearable housing.

17. The electronic device defined in claim 16 wherein the light source comprises a light-emitting diode that is configured to emit the light and wherein the light detector detects the emitted light after the emitted light has reflected from an external object.

18. The electronic device defined in claim 14 further comprising a light source, wherein the light source and the light detector are configured to form a heart rate sensor.

19. The electronic device defined in claim 14 further comprising a housing, a display in the housing, and a wrist band coupled to the housing, wherein the housing has a transparent member and wherein the light detector is configured to detect the light after the light has passed through the transparent member and the ring of optical structures.

20. The electronic device defined in claim 1, wherein each bent light control film in the stack has the same height as the height of the stack and wherein a number of bent light control films in the stack at least partly defines the width of the stack.

* * * * *